(12) United States Patent
Nanba et al.

(10) Patent No.: US 7,186,553 B1
(45) Date of Patent: Mar. 6, 2007

(54) HUMAN DERIVED IMMORTALIZED LIVER CELL LINE

(75) Inventors: Masayoshi Nanba, Okayama (JP); Kenichi Fukaya, Katsuyama (JP); Satoru Asahi, Toyonaka (JP); Sumie Yoshitomi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 09/673,958

(22) PCT Filed: Apr. 27, 1999

(86) PCT No.: PCT/JP99/02224

§ 371 (c)(1),
(2), (4) Date: Aug. 13, 2001

(87) PCT Pub. No.: WO99/55853

PCT Pub. Date: Nov. 4, 1999

(30) Foreign Application Priority Data

Apr. 28, 1998 (JP) .................................. 10-119394

(51) Int. Cl.
C12N 5/08 (2006.01)
C12N 5/00 (2006.01)
C12N 5/02 (2006.01)

(52) U.S. Cl. ....................................... 435/370; 435/325
(58) Field of Classification Search ................ 424/93.2, 424/93.21; 435/325, 366, 370, 455, 456
See application file for complete search history.

(56) References Cited

U.S. PATENT DOCUMENTS 5,506,131 A * 4/1996 Harris et al. ............. 435/240.2
5,660,986 A * 8/1997 Harris et al. .................... 435/6
5,665,589 A * 9/1997 Harris et al. ................. 435/370
5,869,243 A * 2/1999 Jauregui et al. ................ 435/6
6,756,229 B1 6/2004 Nanba et al.

FOREIGN PATENT DOCUMENTS

WO  WO 97/32972  9/1997
WO  WO 98/08935  3/1998

OTHER PUBLICATIONS

Pfeifer et al. PNAS 90:5123-5127, Jun. 1993.*
Kenichi Fukaya et al., "The Way to the Artificial Liver—Advances in Hepatocytes and Bioreactors: Application of Immortalized Human Hepatocytes to the Artificial Liver (Jinkou kanzou heno michi-kansaibou to bioreactor no shimpo: Jinkoukan ni riyousuru saibou—Fushika saibou no riyou)", The Tissue Culture Engineering (Gekkan Soshiki Baiyou Kougaku) vol. 23, No. 8, pp. 292-297 (1997) [with English translation].
M. Jurima-Romet et al., "Evaluation of Drug Interactions in Intact Hepatocytes: Inhibitors of Terfenadine Metabolism", Toxicology in Vitro vol. 10, No. 6, pp. 655-663 (1996).
Masayoshi Nanba, "Development of an Alternative Using Highly Differentiated Cell Population to Animal Experimental Systems—Development of Drug Toxicity Detection System Using Human Hepatocytes in Culture (Koujibunka saibougun ni yoru doubutsu jikken daigae system no kaihatsu-Baiyou hito kansaibou ni yoru yakuzai dokusei kenshutsukei no kaihatsu)", A study of Fundamental Technology for the Development of an Alternative to Animal Experimental Systems (Atarashii Doubutsu Jikkenkei Kaihatsu no tame no Kiban Gijutsu no Kenkyuu), Stage II, 1994-1996, Results Report (1997), pp. 143-147 [with English translation].
Masayoshi Nanba, "Establishment of Cell Lines: 1 Human Cells (Saiboukabu no juritsu: 1 Hito saibou)", Protein, Nucleic Acid and Enzyme, vol. 36, No. 13, pp. 2064-2066 (1991) [with English translation].
Masahiro Miyazaki et al., "Primary Culture of Differentiated Cells: Primary Culture of Liver Parenchymal Cells (Bunka shita saibou no shodai baiyou Kanzou jisshitsu saibou no shodai baiyou)", The Tissue Culture vol. 20, No. 8, pp. 296-301 (1994) [with English translation].
Masayoshi Nanba et al., "A Study of Immortalization of Normal Human Cells Using Chemical Substances and Radiation (Kagaku busshitsu oyobi houshasen ni yoru hito seijou saibou no fushika ni kansuru kenkyuu)", Research on Drug Innovation Project: Drug Innovation Research Report—Stage I Comprehensive Report, pp. 163-165 (1995) [with English translation].
Masahiro Miyazaki et al. "A Study of Liver Cell Culture and Hepatocarcinogenesis (Kansaibou baiyou to kanhatsugan no kenkyuu)", Journal of Medical Association of Okayama (Okayama Igakkai Zasshi) vol. 103, No. 3, pp. 337-347 (1991) [with English translation].
Masahiro Miyazaki et al., "Immortalization of Epithelial-like Cells from Human Liver Tissue with SV40 T-Antigen Gene", Experimental Cell Research vol. 206, No. 1, pp. 27-35 (1993).
Tomokazu Matsuura, "The Way to the Artificial Liver—Advances in Hepatocytes and Bioreactors: Cells Useful for the Artificial Liver -Patenchymal and Non-parenchymal Cells of the Liver- (Jinkou kanzou heno michi—kansaibou to bioreactor no shimpo Jinkoukan ni riyousuru saibou Kanjisshitsu saibou to hijisshitsu saibou)", The Tissue Culture (Gekkan Soshiki Baiyou Kougaku) vol. 23, No. 8, pp. 288-291 (1997) [with English translation].

* cited by examiner

Primary Examiner—Brian Whiteman
(74) Attorney, Agent, or Firm—Mark Chao; Elaine M. Ramesh

(57) ABSTRACT

The present invention relates to a new immortalized hepatocyte culture of human (preferably human fetal) normal cell origin. The immortalized hepatocyte culture of human normal cell origin of the present invention is useful in, for example, screening for compounds or salts thereof having therapeutic/preventive effects on hepatic insufficiency.

1 Claim, 3 Drawing Sheets

HUMAN DERIVED IMMORTALIZED LIVER CELL LINE

This application is the National Phase filing of International Patent Application No. PCT/JP99/02224, filed Apr. 27, 1999.

FIELD OF THE INVENTION

The present invention relates to (1) a new immortalized hepatocyte culture of human (preferably human fetal) normal cell origin, (2) a method of producing said cell culture, (3) a screening method for a compound or a salt thereof ① which inhibits or promotes an enzyme activity involved in the metabolism of xenobiotics in the liver, or ② which inhibits or promotes the expression of a gene encoding an enzyme involved in the metabolism of xenobiotics in the liver, characterized by the use of said cell culture, (4) a compound or a salt thereof ① which inhibits or promotes an enzyme activity involved in the metabolism of xenobiotics in the liver, or ② which inhibits or promotes the expression of a gene encoding an enzyme involved in the metabolism of xenobiotics in the liver, obtained using said screening method, and (5) an analytical method for enzymes involved in the metabolism of xenobiotics and/or endogenous substrates using said cell culture.

BACKGROUND OF THE INVENTION

The hepatocyte possesses numerous physiological functions, including a very important function associated with the metabolism of what is called xenobiotics, wherein drugs, food additives, environmental pollutants and other xenobiotics are metabolized to ready-to-excrete forms. As such, the xenobiotic-metabolizing function sometimes also leads to mutagenesis, toxicity manifestation or substance efficacy manifestation by xenobiotics, and is under very extensive research. For this reason, cultured hepatocytes have been deemed not only to serve as a substitute for laboratory animals, as well as a quick, inexpensive and accurate test method for investigating metabolism in the liver, but also to enable the preparation of what is called artificial liver to substitute for hepatic functions.

However, human normal hepatocytes as isolated from living tissue cannot be subcultured. Cells which can be established as cell cultures often lack the essential differentiating characters; the resulting cell culture often does not accurately reflect the functions of the tissue to which they essentially belong. The class of enzymes involved in the metabolism of what is called xenobiotics in hepatocytes, in particular, lose their activity in a very short time in primary culture; no established cells have been found to sufficiently have the essential characters (J. Dich et al., Hepatology, 8, 39–45 (1988)). Against this background, there has been a wide demand for hepatocytes which have the capability of metabolizing xenobiotics and which permit cultivation. A cell culture of the human liver is prepared by selecting human tumor cells and exemplified by HepG2 (Aden et al., Nature, 282, 615–616, 1979). However, these cells are of tumor cell origin and do not represent immortalized normal cells. To immortalize normal cells, i.e., to allow normal cells to proliferate limitlessly, introduction of the T antigen gene of SV (simian virus) 40 origin, for example, is commonly available. However, no immortalized cell cultures of human hepatic normal parenchymal origin are known to allow observation of the immortalization of normal parenchymal cells of the liver, more specifically enzyme activity involved in the metabolism of xenobiotics, the expression of a gene encoding an enzyme involved in the metabolism of xenobiotics, or the induction of expression of a gene encoding an enzyme involved in the metabolism of xenobiotics. In addition, serum components are essential to media for cultivation of a large number of established cells. This necessity of serum components has been problematic in that not only the stability of cultured cell properties is considerably impeded due to a lack of the qualitative stability of the serum but also the stable, accurate and inexpensive use of established cells is considerably hampered due to the very high price of the serum. Accordingly, proliferation of an established immortalized cell culture in a serum-free medium, while stably retaining its character, would be industrially very beneficial.

DISCLOSURE OF THE INVENTION

The object of the present invention is to provide a cell culture which is derived from human normal hepatocytes (preferably human normal hepatic parenchymal cells), which is capable of proliferating in serum-free complete synthetic media, and which allows the observation of metabolic functions specific to the human liver, more specifically of an enzyme activity involved in the metabolism of xenobiotics, or the expression of a gene encoding an enzyme involved in the metabolism of xenobiotics, and to separate and produce said cell culture.

After extensive investigations in view of the above problem, the present inventors succeeded in establishing a cell culture which is derived from human normal hepatic parenchymal cells, which is capable of proliferating in serum-free complete synthetic media, and which allows the observation of metabolic functions specific to the human liver, more specifically of an enzyme activity involved in the metabolism of xenobiotics, or the expression of a gene encoding an enzyme involved in the metabolism of xenobiotics, made further investigations based on this success, and developed the present invention.

Accordingly, the present invention relates to:

(1) an immortalized hepatocyte cell culture of human normal cell origin having an enzyme activity, involved in the metabolism of xenobiotics or the capability of expressing a gene encoding an enzyme involved in the metabolism of xenobiotics, (2) the cell culture according to the above item (1) above wherein the enzyme activity is NADPH cytochrome P450 reductase activity, glucuronosyl transferase activity, ethoxyresorufine dealkylation activity, benzyloxyresorufine dealkylation activity, pentoxylresorufine dealkylation activity, methoxyresorufine dealkylation activity, flavin monooxygenase activity, epoxy hydratase activity, sulfotransferase activity or glutathione S-transferase activity, (3) the cell culture according to the above item (1) above wherein the enzyme is NADPH cytochrome P450 reductase, cytochrome P450, flavin monooxygenase, epoxy hydratase, glucurosyl transferase, sulfotransferase or glutathione S-transferase, (4) the cell culture according to the above item (3) above wherein the cytochrome P450 is CYP1A1, CYP1A2 or CYP3A, (5) the cell culture according to the above item (1) above wherein the cell culture is FERM BP-6328, (6) a method of producing the cell culture according to the above item (1) above, characterized by introduction of the T antigen gene of SV (simian virus) 40 origin into human normal hepatocytes, (7) the production method according to the above item (6) above wherein the human normal hepatocytes are of human fetal origin, (8) a screening method for a compound or a salt thereof ① which inhibits or promotes an enzyme activity involved in the metabolism of xenobiotics in the liver, or ② which inhibits or promotes the expression of a gene encoding an enzyme involved in the metabolism of xenobiotics in the liver, characterized by the use of the cell culture according to the above item (1) above, (9) a compound or a salt thereof ① which inhibits or promotes an enzyme activity involved in the metabolism of xenobiotics in the liver, or ② which inhibits or promotes the expression of a gene encoding an enzyme involved in the metabolism of xenobiotics in the liver, obtained by using the screening method according to the above item (8) above,

(10) an analytical method for (a) enzymes involved in the metabolism of xenobiotics and/or endogenous substrates, (b) metabolic pathways for xenobiotics and/or endogenous substrates, (c) chemical structures of metabolites of xenobiotics and/or endogenous substrates, (d) inhibition of enzymes which metabolize xenobiotics and/or endogenous substrates, (e) promotion of the activity of enzymes which metabolize xenobiotics and/or endogenous substrates, (f) cytotoxicity due to the metabolism of xenobiotics and/or endogenous substrates, (g) genotoxicity due to the metabolism of xenobiotics and/or endogenous substrates, (h) carcinogenicity due to the metabolism of xenobiotics and/or endogenous substrates, (i) mutagenicity due to the metabolism of xenobiotics and/or endogenous substrates, (j) hepatotoxicity due to the metabolism of xenobiotics and/or endogenous substrates, or (k) hepatic action of xenobiotics and/or endogenous substrates, characterized by the use of the cell culture according to the above item (1) above, and

(11) a method of preparing metabolites of xenobiotics and/or endogenous substrates.

BEST MODES OF EMBODIMENT OF THE INVENTION

Figure 1:
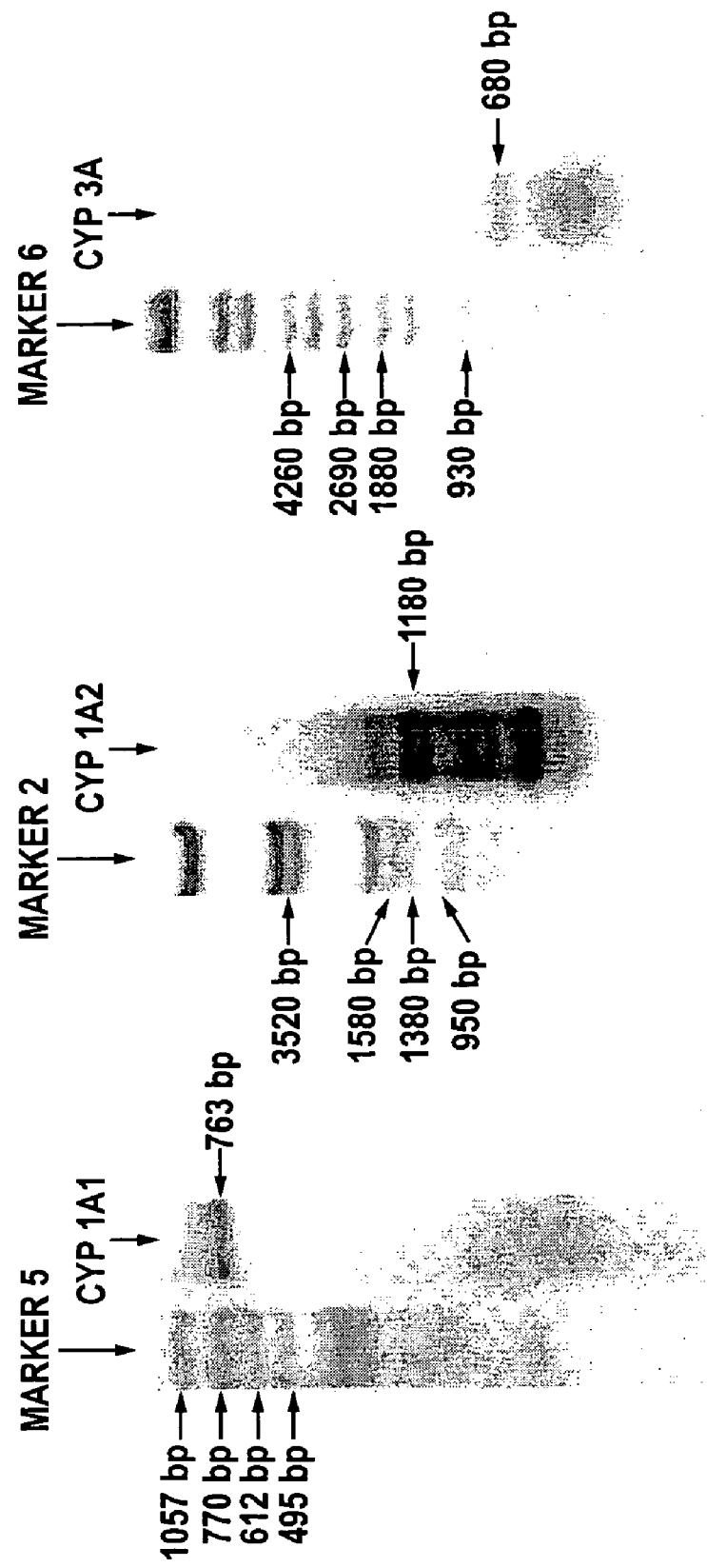
FIG. 1 shows the results of the RT-PCR method performed in Example 3 (electrophoresis diagram), wherein Markers 2, 5, and 6 indicate respective DNA molecular weight markers (manufactured by Nippon Gene).

The term "normal cells", "normal hepatocytes", or "normal tissue" as used herein means cells or tissue which has not cancerated.

In addition, the term "metabolism of xenobiotics" means the metabolism of, for example, a drug, a food additive, an environmental pollutant, or the like, with preference given to drug metabolism etc.

The human normal hepatocytes (preferably human normal hepatic parenchymal cells) used can be separated from normal tissue of human adults, human fetuses, etc. (preferably human fetuses) by a well-established method known as collagenase perfusion. What are called primary cultured cells thus obtained are immortalized in accordance with various commonly known methods etc. Specifically, there may be mentioned a method focusing on the permanent proliferation of tissue which has cancerated wherein individual normal cells are immortalized by transformation with an oncogene introduced therein. Immortalized cell cultures thus established include, for example, subcultures of transformants of animal cells as obtained by introducing an oncogene, such as ras or c-myc, or an oncogene of a DNA type tumor virus, such as adenovirus EIA, SV (simian virus) 40 virus, or human papilloma virus (HPV16), or a tumor antigen (T antigen) gene thereof (E. Ponet et al., Proc. Natl. Acad. Sci., USA, 82, 8503 (1985)). Preferably, the method based on introduction of the T antigen gene of SV40 origin, a modification thereof, or the like can be used (M. Miyazaki et al., Experimental Cell Research, 206, 27–35 (1993)). To culture (subculture) these immortalized hepatocytes, there may be used commonly known culturing methods using known media [e.g., complete synthetic media (preferably serum-free complete synthetic media (e.g., ASF104 medium, Ajinomoto), MEM medium containing about 5 to about 20% fetal bovine serum [Science, Vol. 122, 501 (1952)], DMEM medium [Virology, Vol. 8, 396 (1959)], RPMI 1640 medium [The Journal of the American Medical Association, Vol. 199, 519 (1967)], Williams' medium (Nissui Pharmaceutical), 199 medium [Proceedings of the Society for the Biological Medicine, Vol. 73, 1 (1950)). Complete synthetic media [serum-free complete synthetic media (e.g., ASF104 medium, Ajinomoto)] etc. are particularly preferred. The pH is preferably about 7 to about 7.2. Cultivation is normally carried out at about 37°.

By using a serum-free complete synthetic medium in the process of establishing the immortalized hepatocytes of the present invention, in particular, immortalized hepatocytes capable of proliferating in serum-free complete synthetic media can be obtained.

From among the immortalized hepatocytes thus obtained, those retaining metabolic characteristics specific to the liver, more specifically enzyme activity, enzymes, gene expression and gene expression induction associated with the metabolism of xenobiotics, are selected.

Enzyme activities involved in the liver-specific metabolism of xenobiotics include, for example, NADPH cytochrome P450 reductase activity, glucuronosyl transferase activity, mixed function oxidation (MFO) activities (e.g., ethoxyresorufine dealkylation activity, benzyloxyresorufine dealkylation activity, pentoxylresorufine dealkylation activity, methoxyresorufine dealkylation activity), flavin monooxygenase activity, epoxy hydratase activity, sulfotransferase activity, and glutathione S-transferase activity. Of these activities, NADPH cytochrome P450 reductase activity, glucuronosyl transferase activity, and mixed function oxidation (MFO) activities (e.g., ethoxyresorufine dealkylation activity, benzyloxyresorufine dealkylation activity, pentoxylresorufine dealkylation activity, methoxyresorufine dealkylation activity) are important; NADPH cytochrome P450 reductase activity, in particular, is considered as the most important enzyme activity from the viewpoint of functions in the metabolism of xenobiotics.

Enzymes involved in the liver-specific metabolism of xenobiotics include, for example, NADPH cytochrome P450 reductase, cytochrome P450, flavin monooxygenase, epoxy hydratase, glucurosyl transferase, sulfotransferase, and glutathione S-transferase. Of these enzymes, cytochrome P450 represents the class of enzymes most important from the viewpoint of distribution and functions in the metabolism of xenobiotics. cytochrome P450 is a generic name for a large number of enzymic proteins; CYP1A1, CYP1A2, CYP2A6, CYP2B6, CYP2C8, CYP2C9, CYP2C19, CYP3A (specifically CYP3A4, CYP3A5, CYP3A7 etc.), CYP2D6 etc. are known members of the cytochrome P450 class involved in the metabolism of xenobiotics in the human liver, with CYP1A1, CYP1A2, CYP3A etc. preferably used for the immortalized hepatocyte culture of the present invention. In addition, the functions of cytochrome P450 are also generically called the mixed function oxidation (MFO) and are detected as ethoxyresorufine dealkylation activity, benzyloxyresorufine dealkylation activity, pentoxylresorufine dealkylation activity, methoxyresorufine dealkylation activity etc. Furthermore, the presence of NADPH cytochrome P450 reductase is essential to the expression of the MFO functions of the cytochrome P450 protein; this enzyme can also be classified as an enzyme which metabolizes xenobiotics.

In addition, a large number of xenobiotic-metabolizing enzymes are known to be induced under particular conditions. Well-known examples of this induction include the effects of polycyclic aromatic compounds such as benzpyrene, benzanthracene, 3-methylcholanthrene and dioxin on the expression of CYP1A1 and CYP1A2, the effects of phenobarbitar and phenobarbitone on the induction of CYP2B (e.g., CYP2B6), and the effects of rifampicin, dexamethasone, phenyloin and phenylbutazone on the induction of CYP3A (C. G. Gibson et al., Shinpan Seitaiibutsu no Taishagaku, Kodansha, 1995).

The immortalized hepatocyte culture of human normal cell origin of the present invention can be used to screen for compounds having therapeutic/preventive effects on diseases associated with abnormalities of the metabolism of xenobiotics in the liver (e.g., hepatic insufficiency) because it has ① an enzyme activity involved in the metabolism of xenobiotics in the liver or ② the capability of expressing a gene encoding an enzyme involved in the metabolism of xenobiotics in the liver.

Accordingly, the present invention also provides a screening method for a compound or a salt thereof ① which inhibits or promotes an enzyme activity involved in the metabolism of xenobiotics in the liver, or ② which inhibits or promotes the expression of a gene encoding an enzyme involved in the metabolism of xenobiotics in the liver, characterized in that the test compound is brought into contact with the immortalized hepatocyte culture of human normal cell origin of the present invention, and that observations/measurements are made of changes in ① an enzyme activity involved in the metabolism of xenobiotics in the liver or ② the expression of a gene encoding an enzyme involved in the metabolism of xenobiotics in the liver.

Test compounds include, for example, peptides, proteins, non-peptide compounds, synthetic compounds, fermentation products, cell extracts, plant extracts, animal tissue extracts, and plasma; these compounds may be new compounds or commonly known compounds.

Specifically, the immortalized hepatocyte culture of human normal cell origin of the present invention can be treated with the test compound and compared with an intact control immortalized hepatocyte culture of human normal cell origin to evaluate the therapeutic/preventive effects of the test compound with changes such as those in ① an enzyme activity involved in the metabolism of xenobiotics in the liver or ② the expression of a gene encoding an enzyme involved in the metabolism of xenobiotics in the liver, in said immortalized hepatocyte culture of human origin serving as indices.

Being selected from among the test compounds described above by using the screening method of the present invention, a compound obtained can be used as a safe therapeutic/preventive or other pharmaceutical of low toxicity for diseases associated with abnormalities of the metabolism of xenobiotics in the liver (e.g., hepatic insufficiency) because it has therapeutic/preventive effects on such diseases. Furthermore, a compound derivatized from the aforementioned compound obtained by screening can also be used similarly.

A compound obtained by said screening method may have formed a salt. Said salt is exemplified by salts with physiologically acceptable acids (e.g., inorganic acids, organic acids), bases (e.g., alkali metals), etc., with preference given to physiologically acceptable acid adduct salts. Such salts include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

A pharmaceutical containing a compound obtained by said screening method or a salt thereof can be produced by a commonly known production method or a method based thereon. The preparations thus obtained can be used with, for example, humans or mammals (e.g., rats, mice, guinea pigs, rabbits, sheep, swine, bovines, horses, cats, dogs, monkeys) because they are safe and of low toxicity.

Varying depending on target disease, subject of administration, route of administration, etc., the dose of said compound or a salt thereof is normally about 0.1 to about 100 mg per day, preferably about 1.0 to about 50 mg, and more preferably about 1.0 to about 20 mg, based on the compound, for example, when it is orally administered to an adult (assuming 60 kg body weight) for the purpose of treating hepatic insufficiency. In the case of non-oral administration, although the dose of said compound per administration varies depending on target disease, subject of administration, etc., it is advantageous to administer said compound at about 0.01 to about 30 mg per day, preferably about 0.1 to about 20 mg, and more preferably about 0.1 to about 10 mg, by intravenous injection, for example, when it is administered in the form of an injection to an adult (assuming 60 kg) for the purpose of treating hepatic insufficiency. For other animals, doses converted per 60 kg may be administered.

Examples of dosage forms for the aforementioned preparations include, for example, tablets (including sugar-coated tablets and film-coated tablets), pills, capsules (including microcapsules), granules, fine subtilae, powders, syrups, emulsions, suspensions, injectable preparations, inhalants, and ointments. These preparations are prepared in accordance with commonly known methods (e.g., methods listed in the Japanese Pharmacopoeia).

In such preparations, the content of a compound obtained by the screening method described above or a salt thereof varies depending on the form of the preparation but is normally 0.01 to 100% by weight, preferably 0.1 to 50% by weight, and more preferably 0.5 to 20% by weight, relative to the weight of the entire preparation.

Specifically, tablets can be produced by granulating a pharmaceutical as is, or in a uniform mixture with an excipient, a binder, a disintegrant or other appropriate additives, by an appropriate method, then adding a lubricant etc., and subjecting the mixture to compressive shaping, or by subjecting to direct compressive shaping a pharmaceutical as is, or in a uniform mixture with an excipient, a binder, a disintegrant or other appropriate additives, or subjecting to compressive shaping previously prepared granules as is, or in a uniform mixture with appropriate additives. These tablets may incorporate coloring agents, correctives etc. as necessary, and may be coated with appropriate coating agents.

Injectable preparations can be produced by dissolving, suspending or emulsifying a given amount of a pharmaceutical in an aqueous solvent such as water for injection, physiological saline or Ringer's solution, or a non-aqueous solvent such as a vegetable oil, and diluting to a given amount, or transferring a given amount of a pharmaceutical into a container for injection and sealing the container.

Useful carriers for oral preparations are substances in common use in the field of pharmaceutical formulations, including starch, mannitol, crystalline cellulose, and carboxymethylcellulose sodium. Useful carriers for injection include, for example, distilled water, physiological saline, glucose solutions, and infusion fluids. Other additives in ordinary use in pharmaceutical preparations may also be used as necessary.

Furthermore, the present invention relates to (a) an analytical method for enzymes involved in the metabolism of xenobiotics and/or endogenous substrates, (b) an analytical method for metabolic pathways for xenobiotics and/or endogenous substrates, (c) an analytical method for chemical structures of metabolites of xenobiotics and/or endogenous substrates, (d) a method of preparing metabolites of xenobiotics and/or endogenous substrates, (e) an analytical method for the inhibition of enzymes which metabolize xenobiotics and/or endogenous substrates, (f) an analytical method for the promotion of the activity of enzymes which metabolize xenobiotics and/or endogenous substrates, (g) an analytical method for the detection of cytotoxicity due to the metabolism of xenobiotics and/or endogenous substrates, (h) an analytical method for the detection of genotoxicity due to the metabolism of xenobiotics and/or endogenous substrates, (i) an analytical method for the expression of carcinogenicity due to the metabolism of xenobiotics and/or endogenous substrates, (j) an analytical method for mutagenicity due to the metabolism of xenobiotics and/or endogenous substrates, (k) an analytical method for the expression of hepatotoxicity-due to the metabolism of xenobiotics and/or endogenous substrates, or (l) an analytical method for the hepatic action of xenobiotics and/or endogenous substrates, characterized by the use of the aforementioned immortalized hepatocyte culture of human normal cell origin. The methods (a) through (l) above are described below.

(a) Analytical Method for Enzymes Involved in the Metabolism of Xenobiotics and/or Endogenous Substrates:

For example, by analyzing the structural changes in xenobiotics and/or endogenous substrates caused by exposure of the test substance to immortalized hepatocytes of human normal cell origin, it is possible to analyze the enzymes involved in the metabolism of the xenobiotics and/or endogenous substrates (J. L. Napoli et al., Methods in Enzymology, Vol. 206, pp. 491–501, Ed. by M. R. Waterman et al., Academic Press, 1991; H. K. Kroemer et al., Methods in Enzymology, Vol. 272, pp. 99–198, Ed. by M. R. Waterman et al., Academic Press, 1996). Specifically, such analyses include the identification of enzymes involved in the metabolism of xenobiotics and/or endogenous substrates by analyzing the structural changes in the xenobiotics and/or endogenous substrates due to exposure of the test substance to immortalized hepatocytes of human normal cell origin using inhibitors/antagonists of various enzymes or neutralizing antibodies against various enzymes, and the analysis of enzyme reaction mechanisms and substrate specificity by analyzing the structural changes in xenobiotics and/or endogenous substrates due to exposure of the test substance to cells.

Test substances include, for example, peptides, proteins, non-peptide compounds, synthetic compounds, fermentation products, cell extracts, plant extracts, animal tissue extracts and plasma; these compounds may be new compounds or commonly known compounds.

(b) Analytical Method for Metabolic Pathways for Xenobiotics and/or Endogenous Substrates:

For example, by analyzing the structural changes in xenobiotics and/or endogenous substrates caused by exposure of the test substance to immortalized hepatocytes of human normal cell origin, it is possible to analyze the metabolic pathways for the xenobiotics and/or endogenous substrates (J. L. Napoli et al., Methods in Enzymology, Vol. 206, pp. 491–501, Ed. by M. R. Waterman et al., Academic Press, 1991; H. K. Kroemer et al., Methods in Enzymology, Vol. 272, pp. 99–198, Ed. by M. R. Waterman et al., Academic Press, 1996).

Useful test substances include the same as those mentioned above.

(c) Analytical Method for Chemical Structures of Metabolites of Xenobiotics and/or Endogenous Substrates:

For example, by analyzing the structural changes in xenobiotics and/or endogenous substrates caused by exposure of the test substance to cells, it is possible to analyze the chemical structures of the xenobiotics and/or endogenous substrates (J. L. Napoli et al., Methods in Enzymology, Vol. 206, pp. 491–501, Ed. by M. R. Waterman et al., Academic Press, 1991; H. K. Kroemer et al., Methods in Enzymology, Vol. 272, pp. 99–198, Ed. by M. R. Waterman et al., Academic Press, 1996).

Useful test substances include the same as those mentioned above.

(d) Method of Preparing Metabolites of Xenobiotics and/or Endogenous Substrates:

For example, by collecting conversions (what is called metabolites) of xenobiotics and/or endogenous substrates caused by exposure of the test substance to cells and purifying and separating them by an appropriate method, it is possible to prepare the metabolites of the xenobiotics and/or endogenous substrates (J. L. Napoli et al., Methods in Enzymology, Vol. 206, pp. 491–501, Ed. by M. R. Waterman et al., Academic Press, 1991).

Useful test substances include the same as those mentioned above.

(e) Analytical Method for the Inhibition of Enzymes which Metabolize Xenobiotics and/or Endogenous Substrates:

For example, by exposing the test substance to cells, it is possible to analyze the inhibition of activity of the xenobiotics and/or endogenous substrates (J. L. Napoli et al., Methods in Enzymology, Vol. 206, pp. 491–501, Ed. by M.

R. Waterman et al., Academic Press, 1991). Specifically, detection is possible by the inhibition of cytochrome P450 enzyme activity, a decrease in protein content, a decrease in mRNA, etc. Useful methods of detection include commonly known techniques, such as assays of enzyme activities corresponding to various types of P450, western blotting techniques corresponding to various P450 proteins, northern hybridization techniques corresponding to various types of P450 mRNA, and the RT-PCR method.

Useful test substances include the same as those mentioned above.

(f) Analytical Method for the Promotion of the Activity of Enzymes which Metabolize Xenobiotics and/or Endogenous Substrates:

For example, by exposing the test substance to cells and detecting the increase in the activity of enzymes which metabolize xenobiotics and/or endogenous substrates, the increase in the amount of the enzyme, the increase in the amount of transcription of the gene encoding the enzyme, or the like, it is possible to analyze the promotion of the activity of the xenobiotics and/or endogenous substrates (J. Rueff et al., Mutation Research, 353 (1996), 151–176). Specifically, it is possible by detecting the elevation of cytochrome P450 enzyme activity, an increase in protein content, or an increase in mRNA. Useful methods of detection include commonly known techniques, such as assays of enzyme activities corresponding to various types of P450, western blotting techniques corresponding to various P450 proteins, northern hybridization techniques corresponding to various types of P450 mRNA, and the RT-PCR method.

Useful test substances include the same as those mentioned above.

(g) Analytical Method for Cytotoxicity due to the Metabolism of Xenobiotics and/or Endogenous Substrates:

For example, by exposing the test substance to cells, it is possible to analyze the cytotoxicity due to the metabolism of the xenobiotics and/or endogenous substrates. Specifically, the analysis is achieved by observing cell morphological changes, viable cell count fluctuations, intracellular enzyme leakage, cell surface layer structural changes, intracellular enzyme fluctuations, etc. (D. Wu et al., Journal of Biological Chemistry, 271, (1996), 23914–23919).

Useful test substances include the same as those mentioned above.

(h) Analytical Method for Genotoxicity due to the Metabolism of Xenobiotics and/or Endogenous Substrates:

For example, by exposing the test substance to cells and subjecting the cells to a chromosome aberration test, a micronucleus test, or the like, it is possible to analyze the genotoxicity due to the metabolism of xenobiotics and/or endogenous substrates. Furthermore, the analysis is possible by exposing the test substance to cells and subsequently evaluating the test substance altered by the cells using an appropriate evaluation system for a chromosome aberration test, a micronucleus test, a back mutation test, or the like (J. Rueff et al., Mutation Research, 353 (1996), 151–176; M. E. McManus-et al., Methods in Enzymology, Vol. 206, pp. 501–508, Ed. by M. R. Waterman et al., Academic Press, 1991).

Useful test substances include the same as those mentioned above.

(i) Analytical Method for Carcinogenicity due to the Metabolism of Xenobiotics and/or Endogenous Substrates:

For example, by exposing the test substance to cells and subjecting the cells to a chromosome aberration test, DNA modification, or the like, it is possible to analyze the carcinogenicity due to the metabolism of xenobiotics and/or endogenous substrates. Furthermore, the analysis is possible by exposing the test substance to cells and evaluating the test substance altered by the cells using a carcinogenesis evaluation system with an appropriate chemical substance (J. Rueff et al., Mutation Research, 353 (1996), 151–176; K. Kawajiri et al., Cytochromes P450 metabolic and toxicological aspects, pp. 77–98, Ed. by C. Ioannides, CRC Press, 1996).

Useful test substances include the same as those mentioned above.

(j) Analytical Method for Mutagenicity due to the Metabolism of Xenobiotics and/or Endogenous Substrates:

For example, by exposing the test substance to cells and subjecting the cells to a chromosome aberration test, a micronucleus test, or the like, it is possible to analyze the mutagenicity due to the metabolism of xenobiotics and/or endogenous substrates. Furthermore, the analysis is possible by exposing the test substance to cells and subsequently evaluating the test substance altered by the cells using an appropriate evaluation system for a chromosome aberration test, a micronucleus test, a back mutation test, or the like (J. Rueff et al.,. Mutation Research, 353 (1996), 151–176).

Useful test substances include the same as those mentioned above.

(k) Analytical Method for Hepatotoxicity due to the Metabolism of Xenobiotics and/or Endogenous Substrates:

For example, by exposing the test substance to cells and observing the expression of cytotoxicity, or by exposing the test substance to cells, subsequently administering the test substance altered by the cells to another hepatocyte, a liver section, an extirpated liver, or a laboratory animal, and observing the changes caused thereby in cells, tissue, or living body, it is possible to analyze the hepatotoxicity due to the metabolism of xenobiotics and/or endogenous substrates.

Useful test substances include the same as those mentioned above.

(l) Analytical Method for the Hepatic Action of Xenobiotics and/or Endogenous Substrates:

For example, by exposing the test substance to cells, subsequently administering the test substance altered by the cells to another hepatocyte, a liver section, an extirpated liver, or a laboratory animal, and observing the changes caused thereby in cells, tissue, or living body, it is possible to analyze the expression of the action on the liver.

Useful test substances include the same as those mentioned above.

Abbreviations for bases and others used in the present specification are based on abbreviations specified by the IUPAC-IUB Commission on Biochemical Nomenclature or abbreviations in common use in relevant fields. Some examples are given below.

A: Adenine

T: Thymine

G: Guanine

C: Cytosine

The sequence ID numbers in the sequence listing of the present specification are as follows:

[SEQ ID NO: 1]

Indicates a synthetic primer base sequence used for CYP1A1 in the RT-PCT method performed in Example 3 below.

[SEQ ID NO: 2]

Indicates another synthetic primer base sequence used for CYP1A1 in the RT-PCT method performed in Example 3 below.

[SEQ ID NO: 3]

Indicates a synthetic primer base sequence used for CYP1A2 in the RT-PCT method performed in Example 3 below.

[SEQ ID NO: 4]

Indicates another synthetic primer base sequence used for CYP1A2 in the RT-PCT method performed in Example 3 below.

[SEQ ID NO: 5]

Indicates a synthetic primer base sequence used for CYP3A in the RT-PCT method performed in Example 3 below.

[SEQ ID NO: 6]

Indicates another synthetic primer base sequence used for CYP3A in the RT-PCT method performed in Example 3 below.

The OUMS-29 strain as obtained in Example 1 below has been deposited under the Budapest Treaty and assigned accession number FERM BP-6328 at the National Institute of Bioscience and Human-Technology, Agency of Industrial Science and Technology, Ministry of International Trade and Industry (NIBH) 1–3, Higashi 1-chome, Tsukuba-shi Ibaraki-ken 305-8566 JAPAN since Apr. 21, 1998, and under accession number IFO 50487 at the Institute for Fermentation, Osaka, Foundation (IFO) since Apr. 21, 1998.

The present invention is hereinafter described in detail by means of the following examples, which are not to be construed as limitative. In addition, individual gene manipulations were achieved using the common method described in the manual of Sambrook et al. (Molecular Cloning: A Laboratory Manual, Cold Spring Harbor Laboratory Press) unless otherwise specified.

EXAMPLE 1

Establishment of a Hepatocyte Culture

A well-established method was used to establish an immortalized cell culture by introducing the SV 40 T antigen gene (M. Miyazaki et al., Experimental Cell Research, 206, 27–35 (1993)). The liver was extirpated from a human fetus which died at 21 weeks of gestation; primary cells of hepatic parenchyma were separated by the commonly known collagenase perfusion method. These cells were sown to and cultured on Williams' medium (Nissui Pharmaceutical) supplemented with 10% fetal bovine serum. After 24 hours of cultivation, the SV 40 T antigen gene was introduced by the lipofection method using the plasmid pSV3Neo (P. J. Southern and P. Berg, J. Mol. Appl. Genet., 1, 327–341). For lipofection and subsequent procedures, a serum-free complete synthetic medium (ASF104, Ajinomoto) was constantly used as the culture medium. At 3 days after transfection, passage culture was conducted to promote the growth of hepatocytes, followed by 2 more days of cultivation and selection of neomycin-resistant cells. After 30 days of cultivation, a clone showing evident resistance to G418 was derived and designated as OUMS-29. This clone was believed to have been immortalized because it further grew over 300 generations in the ASF104 medium.

EXAMPLE 2

Determination of the Drug-Metabolizing Enzyme Activity of the OUMS-29 Culture

OUMS-29 cells becoming confluent after 5 to 7 days of cultivation on ASF104 medium were harvested, suspended in 0.1 M phosphate buffer (pH 7.6), and disrupted using an ultrasound generator; this suspension was used as the enzyme source to determine enzyme activity as described below.

(1) Cytochrome P450 Reductase Activity

Determinations were made basically by the method described in Biological Pharmacology, 37, 4111–4116, 1988. Specifically, cytochrome P450 reductase activity was determined on the basis of cytochrome C reduction in the presence of NADPH (reduced nicotinamide adenine dinucleotide phosphate) and an enzyme source of OUMS-29 origin with cytochrome C as the substrate. As a result, the enzyme source of OUMS-29 culture origin exhibited an enzyme activity of 8 units, taking the activity for reducing 1 nanomol of cytochrome C per milligram of protein per minute as 1 unit.

(2) Glucurosyl Transferase Activity

Determinations were made basically by the method described in Biological Pharmacology, 37, 4111–4116, 1988. Specifically, the amount of 1-naphthol glucuronide produced was determined in the presence of UDP-glucuronic acid (Sigma) and an enzyme source of OUMS-29 origin with 1-naphthol (Sigma) as the substrate. As a result, the enzyme source of OUMS-29 culture origin exhibited an enzyme activity of 196 units, taking the activity for producing 1 picomol of 1-naphthol glucuronide per milligram of protein per minute as 1 unit.

(3) Mixed Function Oxidation (MFO) Activity

Determinations were made basically by the method described in Biological Pharmacology, 42, 1307–1313, 1991. Specifically, the amount of product resulting from dealkylation of each substrate was determined in the presence of NADPH and an enzyme source of OUMS-29 origin with ethoxyresorufine (Sigma), pentoxyresorufine (Sigma), benzyloxyresorufine (Sigma) and methoxyresorufine (Sigma) as the substrates. As a result, the enzyme source of OUMS-29 culture origin exhibited enzyme activities of 0.25 units for ethoxyresorufine as the substrate, 0.47 units for pentoxyresorufine as the substrate, 0.38 units for benzyloxyresorufine as the substrate, and 0.32 units for methoxyresorufine as the substrate, respectively, taking the activity for producing 1 picomol of product per milligram of protein per minute as 1 unit.

EXAMPLE 3

Expression of the Cytochrome P450 Gene

The expression of cytochrome P450 in the OUMS-29 culture can be analyzed by assessing the level of mRNA content by the commonly known RT-PCR method using DNA primers specific to different types of cytochrome P450. These primers can be prepared from the sequences of the respective types of cytochrome P450 available from the Gene Bank database. The accession numbers at the Gene Bank are K03191 for CYP1A1, M55053 for CYP1A2, J02625 for CYP2E1, J04449 for CYP3A4, J04813 for CYP3A5, and D00408 for CYP3A7. The individual primers used were 5'-ATGCTTTTCC CAATCTCCAT GTGC (SEQ ID NO:1) and 5'-TTCAGGTCCT TGAAGGCATT CAGG (SEQ ID NO:2) for CYP1A1, 5'-GGAAGAACCC GCACCTGGCA CTGT (SEQ ID NO:3) and 5'-AAACAGCATC ATCTTCTCAC TCAA (SEQ ID NO:4) for CYP1A2 and 5'-ATGGCTCTCA TCCCAGACTT G (SEQ ID NO:5) and 5'-GGAAAGACTG TTATTGAGAG A (SEQ ID NO:6) for CYP3A.

Regarding annealing conditions for the RT-PCR method, the annealing temperatures were 55° C. for CYP1A1, 65° C. for CYP1A2, 55° C. for CYP3A, and 65° C. for CYP2E1, the cycle numbers being 28 to 36 cycles.

The OUMS-29 culture was cultured for 5 to 7 days; the cells becoming confluent were harvested, from which RNA was extracted using the RNAeasy kit (Quiagen). This RNA, along with the previously determined primers specific to the respective types of cytochrome P450, was subjected to reverse transcription from mRNA and PCR using an one-step PCR kit (Takara Shuzo), after which it was separated using agarose gel and visualized with ultraviolet rays in the presence of ethidium bromide. The results are shown in FIG. 1. Signals were detected at positions near 763 bp, predicted for CYP1A1, 1180 bp, predicted for CYP1A2, and 680 bp, predicted for CYP3A; the expression of the corresponding genes in the OUMS-29 culture was verified.

EXAMPLE 4

Induction of Expression of the Cytochrome P450 Gene

Figure 2:
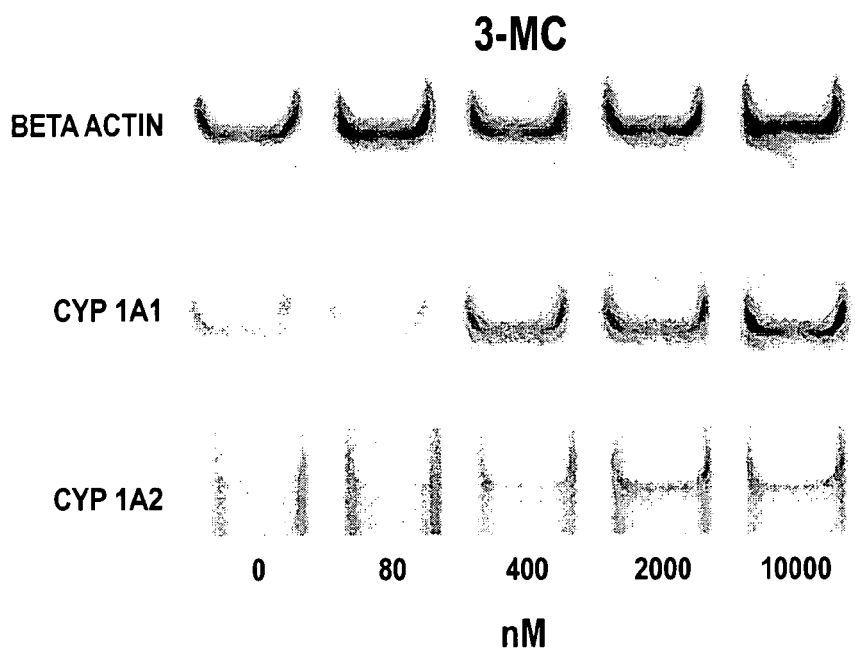
FIG. 2 shows the results of the RT-PCR method after addition of 3-methylcolanthrene (3-MC) performed in Example 4.
Figure 3:
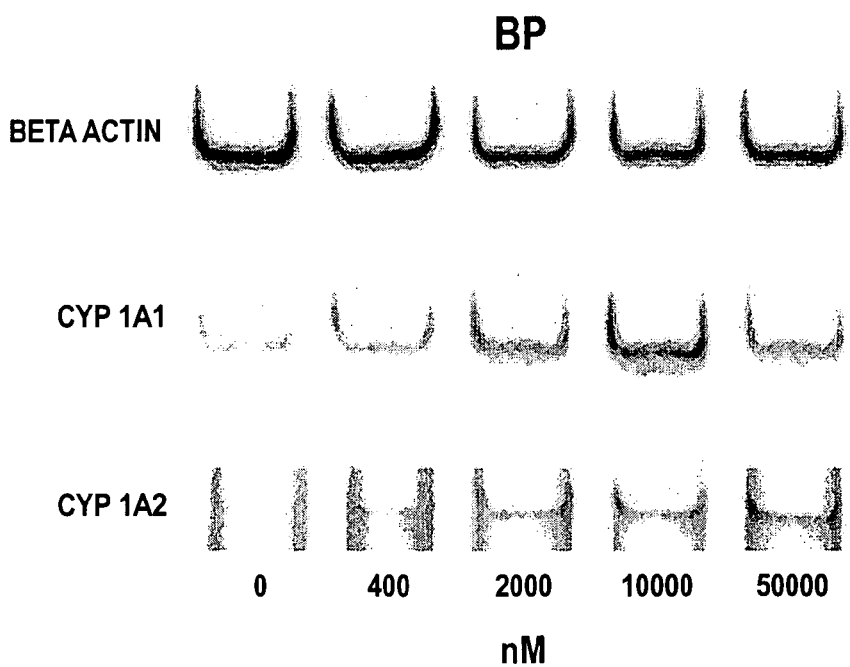
FIG. 3 shows the results of the RT-PCR method after addition of benzpyrene (BP) performed in Example 4.
Figure 4:
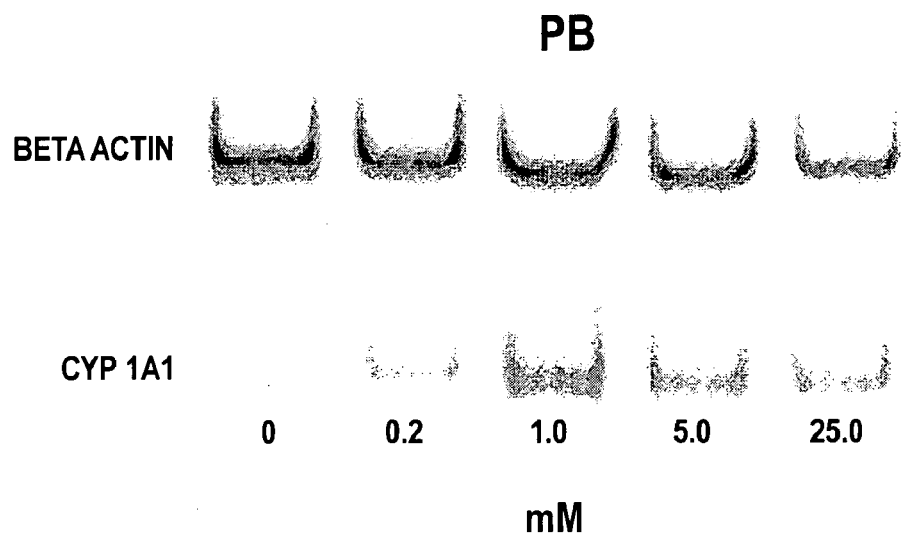
FIG. 4 shows the results of the RT-PCR method after addition of phenobarbitone (PB) performed in Example 4.
Figure 5:
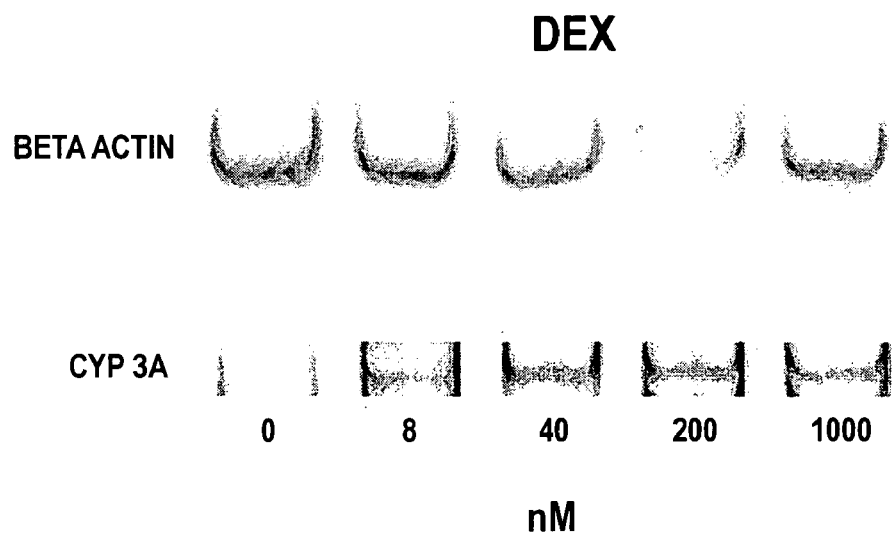
FIG. 5 shows the results of the RT-PCR method after addition of dexamethasone (DEX) performed in Example 4.

To OUMS-29 cells becoming confluent after cultivation for 5 to 7 days, 3-methylcholanthrene (3-MC) at final concentrations of 0 to 10000 nM (FIG. 2), 0 to 50000 nM benzpyrene (BP) (FIG. 3), 0 to 25 mM phenobarbitone (PB) (FIG. 4), or 0 to 1000 nM dexamethasone (DEX) (FIG. 5) was added, followed by cultivation for 1 more day. The cultured cells were separated, from which RNA was extracted using the method described above and subjected to RT-PCR.

Regarding annealing conditions for the RT-PCR method, the annealing temperatures were 55° C. for CYP1A1, 65° C. for CYP1A2, and 55° C. for CYP3A, the cycle numbers being 28 to 36 cycles.

The cycle number for beta-actin, serving as a control, was 15 cycles.

In this operation, an actin competitive RT-PCR kit (Takara Shuzo) was used to correct the total mRNA content in each sample with reference to the mRNA content of beta-actin, which is expressed to the same extent in all tissues. The results are shown in FIGS. 2 through 5. The expression of CYP1A1 was enhanced by the addition of 3-methylcholanthrene, benzpyrene, and phenobarbitone, the expression of CYP1A2 by the addition of 3-methylcholanthrene and benzpyrene, and the expression of CYP3A by the addition of dexamethasone; the OUMS-29 culture was verified to be capable of expressing the gene encoding cytochrome P450.

INDUSTRIAL APPLICABILITY

The immortalized hepatocyte culture of human normal cell origin of the present invention, i.e., an immortalized hepatocyte culture of human origin which retains an enzyme activity involved in the metabolism of xenobiotics or the capability of expressing a gene encoding an enzyme involved in the metabolism of xenobiotics, is useful in screening for, for example, compounds having therapeutic/preventive effects on hepatic insufficiency or salts thereof.

The invention claimed is:

1. An immortalized hepatocyte cell culture of human normal cell origin retaining CYPIA1, CYPIA2 and CYP3A enzyme activity involved in the metabolism of xenobiotics in the liver or which can be induced to express genes encoding enzymes involved in the metabolism of xenobiotics in the liver, wherein said enzymes are CYPIA1, CYPIA2 and CYP3A wherein the cell culture is FERM BP-6328.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Synthetic primer base sequence used for CYP1A1
      in the RT-PCT method performed in Example 3.

<400> SEQUENCE: 1
atgcttttcc caatctccat gtgc                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic primer base sequence used for CYP1A1
      in the RT-PCT method performed in Example 3.

```
<400> SEQUENCE: 2
ttcaggtcct tgaaggcatt cagg                                              24

<210> SEQ ID NO 3
<211> LENGTH: 24
<212> TYPE: DNA
<213> ORGANISM: Artificial Sequence
<220> FEATURE:
<223> OTHER INFORMATION: Synthetic primer base sequence used for CYP1A2
      in the RT-PCT method performed in Example 3.

<400> SEQUENCE: 3
ggaagaaccc gcacctggca ctgt                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic primer base sequence used for CYP1A2
      in the RT-PCT method performed in Example 3.

<400> SEQUENCE: 4
aaacagcatc atcttctcac tcaa                                              24

<210> SEQ ID NO 5
<211> LENGTH: 21
<212> TYPE: DNA
<213> ORGANISM: Artificial Sequence
<220> FEATURE:
<223> OTHER INFORMATION: Synthetic primer base sequence used for CYP3A
      in the RT-PCT method performed in Example 3.

<400> SEQUENCE: 5
atggctctca tcccagactt g                                                 21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer base sequence used for CYP3A
      in the RT-PCT method performed in Example 3.

<400> SEQUENCE: 6
ggaaagactg ttattgagag a                                                 21
```